United States Patent [19]

Siegel et al.

[11] 4,323,582

[45] Apr. 6, 1982

[54] METHOD OF TREATING ANIMALS AND HUMANS FOR INTERNAL AND EXTERNAL PARASITES

[76] Inventors: Norman H. Siegel, 3956 Farragut St., Hollywood, Fla. 33021; Dan C. Roehm, 808 NE. 20th Ave., Fort Lauderdale, Fla. 33304

[21] Appl. No.: 170,621

[22] Filed: Jul. 21, 1980

[51] Int. Cl.³ .................................................. A01N 33/02
[52] U.S. Cl. ............................. 424/325; 424/DIG. 10
[58] Field of Search .......................... 424/325, DIG. 10

[56] References Cited

U.S. PATENT DOCUMENTS 2,383,564  8/1945  Ralston et al. ....................... 424/325
3,826,842  7/1974  Bordenca et al. ........... 424/DIG. 10

FOREIGN PATENT DOCUMENTS 50-40727  4/1975  Japan .
50-48126  4/1975  Japan .
50-58227  5/1975  Japan .

OTHER PUBLICATIONS

Soap & Sanitary Chemicals, Mar. 1952 pp. 136 & 137.
King; Chemicals Evaluated as Insecticides and Repellents at Orlando, Fla., pp. 13–16, 91, 165, 279, 281, 282 & 333 (1954).

*Primary Examiner*—Allen J. Robinson
*Attorney, Agent, or Firm*—Murray and Whisenhunt

[57] ABSTRACT

A method for treating animals, including humans, suffering from blood sucking internal and external insect infestation is provided by administering orally or topically a lower alkanolamine, e.g., mono-, di- or triethanolamine.

11 Claims, No Drawings

METHOD OF TREATING ANIMALS AND HUMANS FOR INTERNAL AND EXTERNAL PARASITES

The present invention relates to a method of treating animals having therein or topically disposed thereon an infestation of blood sucking parasites, e.g., intestinal parasites, fleas, ticks, and the like. More particularly, the invention relates to such method of treatment wherein the animal is dosed with an effective amount of a lower alkanolamine.

BACKGROUND OF THE INVENTION

Blood sucking parasitic infestation on animals has been a continued problem in the art. While the variety of the blood sucking parasitic infestation varies in different parts of the world, e.g., lice, ticks, fleas, mosquitoes, tsetse flies and the like, all of these blood sucking infestations share the common hazard of a potential for spreading of disease. Accordingly, considerable effort has been expended in the art to control such parasitic infestations on animals. None of these methods known to the prior art have been entirely satisfactory.

One method of controlling such topical parasitic infestation is that of applying a liquid to the animal in the form of a shampoo, kip or spray, wherein the liquid contains ingredients which are toxic to the parasites. Notable among the ingredients of such liquid preparations are petroleum distillates and coal tar derivatives, such as cresol. Such liquid preparations are, however, inconvenient to apply and represent a substantial hazard to the animal, particularly in regard to accidental ocular contamination. This is particularly true since these liquids must be copiously applied to the animal.

Another approach is to dust the animal with an insecticide containing dust, e.g., a dust containing Carboril. While this method is more convenient and in many cases more effective than the liquid preparations, the dust is relatively easily removed and must be relatively frequently applied. Additionally, while such insecticides are generally safe, they do present a level of toxicity to the animal and free use thereof cannot be continued with impunity. Further, with continued use, many insects, through evolution, develop immunities to those insecticides and the effectiveness thereof in the dusting powder considerably decreases.

Another approach in the art is to apply to the animal a solid plastic material containing a vaporizable insecticide. This solid plastic, referred to as a generator, continously releases vaporizable insecticide and the vapors, next to the animal bodies, will control the insect infestation. However, this method in the art is only partially successful, since the vapors rapidly dissipate in air and for larger animals the concentration of the insecticide vapor around the entire body is not sufficient for control of insect infestation.

Intestinal and urinary parasites are treated with a variety of medicines, but these are generally not only toxic to the parasite, but have some considerable toxicity to the animals.

Accordingly, it would be a substantial advantage in the art to provide a method of treatment of animals suffering from blood sucking parasitic infestation wherein the treatment is convenient to use, is essentially non-toxic to the animals, will control parasitic infestation over and in the entire body of the animal and does not cause evolutionary changes in the parasites whereby immunity ultimately results.

OBJECTS OF THE INVENTION

Accordingly, it is therefore an object of the invention to provide a method for the treatment of animals suffering from blood sucking parasitic infestation wherein the foregoing desired characteristics are achieved. It is another object of the invention to provide such treatment wherein the application of the treatment itself is neither harmful to the animal or to the human applicator, when the animal is not a human. It is a further object of the invention to provide such method which is suitable for use, for example, by a householder without any experience in carrying-out the treatment and wherein carrying-out the treatment is not hazardous to the householder. Other objects will be apparent from the following description and claims.

BRIEF DESCRIPTION OF THE INVENTION

The invention is based on several primary discoveries. The first and most basic discovery is that lower alkanolamines have the unexpected property of effecting a condition in the skin or tissues of animals which makes the skin or tissues unattractive to blood sucking parasites. This discovery was surprisingly made while performing animal testing of certain known alkanolamines in connection with the treatments disclosed and claimed in U.S. Pat. Nos. 3,906,109, and 3,892,855. Those prior patents relate to the use of lower alkanolamine for effective blood clotting depressant therapy and the control of lipids in the blood stream, respectively. It was unexpectedly and surprisingly observed in those further animal tests that the test animals, over a period of time, became devoid of blood sucking parasitic infestation.

As a subsidiary discovery to the above, it was found that blood sucking parasites on animals being treated with the lower alkanolamine, most surprisingly, while being present on the animal did not bite the animal and suck blood therefrom. Eventually, the parasites simply die from lack of nutrition (i.e., blood sucked from the animal) or dropped off of the animal prior to dying.

The third discovery was that the lower alkanolamine therapy for control of blood sucking parasitic infestation was effective by a wide variety of modes of administration. Thus, the lower alkanolamine could be administered through an orifice of the body, e.g., orally, or by injection, or by topical application. Apparently, irrespective of the mode of administration, the lower alkanolamine has the property of ultimately causing substantial residues of the lower alkanolamine in the dermis or epidermis or the fatty tissue immediately thereunder. It is also apparent that in topical administration, the lower alkanolamine penetrates the skin and achieves the same residence in or under the skin. The presence of the lower alkanolamine in or under the skin makes the skin of the animal unattractive for biting by the blood sucking parasites and the parasites do not bite the animal. Hence, the parasites die of lack of nutrition or simply abandon the animal. Since the parasites do not ingest the alkanolamine, at least to any great extent, no evolutionary resistance to this therapy is observed. A similar result is observed with intestinal or urinary tract parasites.

Accordingly, broadly stated, there is provided a method for treating animals suffering from blood sucking parasitic infestation comprising administering to the animal a said parasitic repugnant effective amount of a lower mono- di- or tri-alkanolamine or an at least partially neutralized form thereof.

DETAILED DESCRIPTION OF THE INVENTION

As noted above, the alkanolamine useful in the present invention is a lower mono-, di- or tri-alkanolamine, which is defined as:

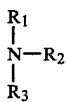

where $R_1$, $R_2$ and $R_3$ are lower alkanol of up to 6 carbon atoms and having up to three OH groups on each alkanol group or hydrogen or lower alkyl (including unsaturate alkyl, e.g., alkenyl) of up to 6 carbons, which may be unsubstituted or substituted, provided that not more than two of the R groups are hydrogen or lower alkyl. The alkyl may be substituted, for example, with aryl, e.g., benzene and toluene, although no substitution is required and the particular substitution is not critical.

Preferably, the lower alkanolamine has from 2 to 6 carbon atoms and more preferably is at least one member selected from the group of monoethanolamines, diethanolamines and triethanolamines. These amines are known to the art and the above-noted preferred embodiments are commercially available.

Is is preferred that the lower alkanolamine be administered to the animal in essentially the neutralized form, i.e., a pH of between about 4 and 8. Thus, the neutralization of the amine is carried out in a conventional manner with conventional non-toxic neutralizing agents. Among others, the neutralizing agent may be an acid such as a mineral acid, e.g., hydrochloric acid, nitric acid and sulfuric acid, or an organic acid such as acetic acid, citric acid, tartaric acid, lactic acid, ascorbic acid, methanesulfonic acid, ethanesulfonic acid, quinic acid, 3-hydroxy-2-naphthoic acid, naponic acid (1,5-naphthalenedisulfonic acid), acetylsalicylic acid, salicyclic acid, mucic acid, muconic acid and the like.

Of course, bases may be used to adjust the pH, such as food-grade bases, e.g., sodium hydroxide, potassium hydroxide and the like. In any event, the amine may be used in the unneutralized form or in the at least partially neutralized form, i.e., the form having a pH of between 4 and 8 and more preferably between 6 and 8 and ideally either a pH of 7 or slightly above. The neutralization is simply achieved by mixing the amine with the appropriate neutralization agent and monitoring the pH until the desired pH is reached.

The administration of the amine may be by introduction into a body orifice, more usually oral administration. Thus, the amines are prepared for administration either as a solution, suspension or elixir, or as a tablet, torche, capsule or the like. The amines may be mixed with any desired inert diluent, extender, carrier, tableting powder, etc., but the amines, normally, will be the only active ingredient. Thus, in this specification and claims, the definition of "consisting essentially of" is that the compositions to be administered are composed only of inert ingredients and the present active amines.

Alternatively, the administration may be intravenously, subcutaneously, topically or intramuscularly. However, it is preferred that the administration be either orally or topically. When the administration is intravenously, subcutaneously or intramuscularly, conventional diluents are normally used, e.g., physiological saline solution and the like. When the administration is topically, similar diluents may be used, although the amine may be compounded in conventional topical carriers, such as the conventional dermatological creams, ointments, salves and the like, all of which are well known to the art and need not be detailed herein for purposes of conciseness.

For oral administration, the dosage, based on the amine, may be from as little as 0.1 cc to as much as 3 cc, per 150 kilogram of body weight, on an undiluted bases. But more usually the dosage will be between 0.3 cc and 1.5 cc. A lower dosage, e.g., 0.1 cc to 2 cc will be used with intravenous, subcutaneous or intramuscular administration. On the other hand, for topical administration, all areas of the skin having parasitic infestations, and more preferably all of the skin area, must be contacted with the amine. While this topical application can be with the amine in undiluted form, for ease of application it is normally diluted whereby the amine is from 1 to 50% by weight of the diluent, the diluent being one of the diluents noted above, or simply water, or one of the dermalogical preparations noted above. Of course, where the animal skin is usually susceptible only in part to parasitic infestation, i.e., where the skin does not contain substantial amounts of hair except in defined areas, such as a human. The dosage of the topical application is sufficient to contact essentially all skin covered by substantial amounts of hair.

Irrespective of the mode of administration, in order to insure that a repugnant effective amount of the amine is present, the administration is performed at least weekly until the parasitic infestation is substantially eliminated. More preferably, administration is at least twice a week and up to daily. With such frequencies of administration, the parasites of the infestation will slowly die or abandon the body, for the reasons noted above. This death or abandonment will usually take place in about 2 to 4 weeks, from the onset of administration, although with lower dosages and larger animals, this time period for death or abandonment by the parasites may be 3 to 6 weeks. In any event, the administration is continued until the parasitic infestation is substantially eliminated. Thereafter, continued dosing will insure freedom from such parasitic infestation. As can be appreciated, this is particularly important in connection with parasitic infestations of fleas and ticks, e.g., for dogs, since dogs are normally continually exposed to those insects and the infestation may occur at any time.

For treatment of internal parasites, e.g., tape worms, hook worms, and other internal parasites, the dose is usually 5-40 cc, e.g., 15 cc/100 lbs. weight, for at least 3 consecutive days. This dose induces bowel movements which release the parasites with the excrement.

Dosage for either mode of administration is not narrowly critical. It appears that the alkanolamine has a residence time either in or on the body. Thus, even when low dosages are used, with continued dosing, required concentrations of the alkanolamine will be built in or on the body. Hence, any convenient concentration of the alkanolamine in the administration composition is suitable for purposes of this treatment.

The treatment is equally useful for birds and reptiles. Thus, the term "animal" as used in the specification and claims is intended to include birds and reptiles.

The treatment of the present invention is applicable to any animal, including humans. Alkanolamines of the present type have been administered to humans for other reasons and those administrations have shown no toxicity or adverse side effects. For example, triethanolamine has been used as an inactive carrier for Folbesyn for intravenous administration, and diethanolamine has been used as an intravenous carrier for Grantrisin (see Physician's Desk Reference, 33rd Edition 1979). In addition, an oral preparation known as Persantine or Dipyridmose contains 40% of diethanolamine. These carriers have been known as inactive and innocuous carriers for human use. Other uses for these amines as carriers and preparations for human treatment are also known. Indeed, triethanolamine is available in USP Grade, which grade includes some diethanolamine and some small amounts of monoethanolamine. In addition, triethanolamine has been used in formulation of dermatologic medicaments and cosmetic creams (see Pharmaceutical Recipe Book, 3rd Edition, 1943, for typical formulas).

The invention will be illustrated by the following examples, but it is to be understood that the invention is not limited thereto and extends to the scope of the foregoing description and following claims. In the examples, as well as in the specification and claims, all percentages and parts are by weight unless otherwise indicated.

EXAMPLE I

Approximately equal molar amounts of sulfuric acid and hydrochloric acid were combined and diluted to approximately a one normal combined acid. The combined diluted acid was slowly added to triethanolamine (USP) until a pH of approximately 7 was obtained, thereby preparing the neutralized triethanolamine.

A portion of the so prepared neutralized triethanolamine was diluted with water to 10% neutralized triethanolamine to prepare a dog dip. A 95-pound mongrel dog with heavy flea infestation was successfully treated with that dip.

Another portion of the neutralized triethanolamine was used for oral administration to the dog. 28 drops of the neutralized triethanolamine was orally administered to the dog each day for 7 days, and 14 drops were orally administered each day thereafter. After approximately 2 weeks, the flea infestation had been reduced to approximately 90% and the remaining fleas were noticeably flatter in their abdomens, which indicated starvation and dehydration of the fleas. No blood was found on compressing the fleas between glass slides. The dog was then placed in a flea-infested environment and a subsequent inspection of the dog showed considerable flea infestation. After removing the dog from the flea-infested environment, the infestation of fleas was considerably reduced and an examination of remaining fleas showed the same evidence of starvation and dehydration.

EXAMPLE II

Diethanolamine was mixed with hydrochloric acid until the diethanolamine was neutralized, i.e., a pH of approximately 7.

A 75-pound Doberman Pinscher with severe chronic flea infestation was examined and determined to have an excess of 200 fleas on its body. 30 drops of the neutralized diathanolamine was orally administered to the dog each day by mixing with the dog's food. At the end of 2 weeks of daily administration, the flea infestation was examined and was found to have decreased by approximately 90%. The remaining fleas exhibited the same evidence of starvation and dehydration as that explained in Example I. There was no evidence of fresh flea bites and the fleas seemed to lose motorability and were listless.

EXAMPLE III

A 35-pound mixed-breed dog had heavy flea infestation and had become allergic to conventional flea powder. Cortisone had been used to mitigate the effects of the allergy, but only limited use of the flea powder was permissible. Accordingly, the flea infestation could not be controlled.

14 drops of a 43% solution of diethanolamine, prepared in the manner described in Example II, were administered orally, daily, to the dog. At the end of 2 weeks, the flea infestation was still considerable and the dosage per day was doubled. After an additional 2 weeks, the Cortisone could be discontinued and the flea infestation was essentially eradicated. Thereafter, flea infestation was avoided by a maintenance dosage of 14 drops of the diethanolamine solution per day.

EXAMPLE IV

Neutralized mono-isopropanolamine was prepared in the manner described in Example I. 6 mols of the mono-isopropanolamine was administered orally, daily, to a 50-pound mongrel with heavy infestation of mites (mange), fleas and ticks. Within several days, ticks could be visually observed abandoning the dog. Within about 2 weeks, the mange had bee cleared and the flea infestation was essentially eliminated.

EXAMPLE V

Three dogs were determined to have heavy infestation of hookworm. After 2 weeks of oral administration, daily, of 3 to 6 millimols of neutralized diethanolamine, prepared as in Example II, the animal's stools were re-examined and no evidence of hookworm was present. Hookworms, are, of course, a blood sucking parasite which reside in the animal's digestive tract. This example shows that the insect infestation may be internal, as well as external. Similar tests were done on dogs with tapeworms and similar results were obtained.

EXAMPLE VI

Both of the alkanolamines of Example I and Example II were applied topically to human test subjects on one arm, and plain water was applied to the other arm of each of the test subjects. Both arms were simultaneously exposed to hungry mosquitoes. While the mosquitoes equally congregated on both arms and remained on both arms, the mosquitoes uniformly refused to bite the arm treated with the alkanolamines, while quickly biting the untreated arm.

From the above, it can be appreciated that the alkanolamine does not function as a repellant, since upon application the parasites do not immediately shun or abandon the animal. The alkanolamine simply makes the animal repugnant to biting by parasites, and, in due course, the parasites abandon the animal, or die, by reason of lack of nutrition. Thus, the alkanolamines are parasite repugnances and in dosing a parasitic repugnant effective amount is used.

What is claimed is:

1. A method of treating animals suffering from blood-sucking parasitic infestation comprising:
   administering orally or by injection to said animals a non-toxic parasitic repugnant effective amount of a lower alkanolamine selected from the group consisting of mono-ethanolamine, diethanolamine tri-ethanolamine and an at least partially neutralized form thereof having a pH of between 4 and 8.

2. The method of claim 1 wherein the administration is by introduction into a body orifice.

3. The method of claim 2 wherein the administration is orally.

4. The method of claim 1 wherein the administration is intraveneously, subcutaneously, or intramuscularly.

5. The method of claim 3 wherein the dosage is from 0.1 cc to 3.00 cc per 150 Kg body weight, on an undiluted basis.

6. The method of claim 4 wherein the dosage is from 0.1 cc to 2 cc per 150 Kg body weight, on an undiluted basis.

7. The method of claim 1 wherein the amine is in an essentially neutralized form having a pH of between 6 and 8.

8. The method of claim 1 wherein the amine is in a diluted form.

9. The method of claim 8 wherein the diluent is a pharmaceutically acceptable diluent.

10. The method of claim 1 wherein the treatment is administered at least weekly until the parasitic infestation is substantially eliminated.

11. The method of claim 1 wherein the parasitic infestation is that of at least one of fleas, ticks, mites, and worms.

* * * * *